(12) United States Patent
Levin et al.

(10) Patent No.: US 7,189,351 B2
(45) Date of Patent: Mar. 13, 2007

(54) D-TAGATOSE AS AN ANTI-BIOFILM AGENT

(75) Inventors: Gilbert V. Levin, Annapolis, MD (US); Yongming Lu, Clarksville, MD (US)

(73) Assignee: Spherix Incorporated, Beltsville, MD (US)

( * ) Notice: Subject to any disclaimer, the term of this patent is extended or adjusted under 35 U.S.C. 154(b) by 569 days.

(21) Appl. No.: 10/223,480

(22) Filed: Aug. 20, 2002

(65) Prior Publication Data
US 2003/0103912 A1    Jun. 5, 2003

Related U.S. Application Data

(63) Continuation-in-part of application No. 09/983,795, filed on Oct. 25, 2001.

(60) Provisional application No. 60/356,753, filed on Feb. 15, 2002.

(51) Int. Cl.
*B14J 14/00* (2006.01)
*A61K 31/7004* (2006.01)

(52) U.S. Cl. .......................... 422/43; 514/23
(58) Field of Classification Search ............... 514/23; 536/1.1; 424/439, 440; 422/43
See application file for complete search history.

(56) References Cited

U.S. PATENT DOCUMENTS 4,428,935 A * 1/1984 Myers .................... 424/114
4,786,722 A * 11/1988 Zehner ................... 426/658
5,447,917 A    9/1995 Zehner et al.
6,015,793 A    1/2000 Levin
6,225,452 B1   5/2001 Levin
6,267,897 B1   7/2001 Robertson et al.

FOREIGN PATENT DOCUMENTS

WO         WO 99/43217      *  2/1999

OTHER PUBLICATIONS

Bertelsen et al., Food Science and Technology, vol. 112, 2001.*
Shaniztki et al., "Identification of Fusobacterium nucleatum PK 1594 Glactose-Binding Adhesin Which Mediates Coaggregation with Periopathogenic Bacteria and Hemagglutination", Infect. Immun., 65:5231-5237, 1997.
Kolenbrander et al., "Inhibition of Coaggregation between Fusobacterium nucleatum and Porphyromonas (Bacteroides) gingivalis by Lactose and Related Sugars", Infect. Immun., 57:3204-3209, 1989.
Paul E. Kolenbrander et al., "Inhibiton of Coaggregation between Fusobacterium nucleatum and Porphyromonas (Bacteroides) ginivalis by Lactose and Related Sugars", Laboratory of Microbial Ecology, National Institute of Dental Research, Bethesda, MD, vol. 57, No. 10, pp. 3204-3209.
Bertelsen et al., "Tagatose", Food Science and Technology, vol. 12, pp. 105-127, 2001.

* cited by examiner

*Primary Examiner*—Leigh C. Maier
(74) *Attorney, Agent, or Firm*—Roylance, Abrams, Berdo & Goodman, L.L.P.

(57) ABSTRACT

There is disclosed a method for disrupting biofilm and for inhibiting biofilm formation in an aqueous environment that comprises contacting said environment with an effective amount of D-tagatose.

2 Claims, No Drawings

D-TAGATOSE AS AN ANTI-BIOFILM AGENT

CROSS-REFERENCE TO RELATED APPLICATIONS

This application claims the benefit under 35 U.S.C. § 119(e) of Provisional Application No. 60/356,753, filed Feb. 15, 2002, for "Chewing Gum Containing D-Tagatose As An Anti-Biofilm Agent, which is hereby incorporated by reference in its entirety. This application is also a continuation-in-part application of U.S. application Ser. No. 09/983,795, filed Oct. 25, 2001 for "D-Tagatose As An Anti-Biofilm Agent, which application is hereby incorporated by reference in its entirety.

BACKGROUND OF THE INVENTION

This invention relates to the use of D-tagatose, such as in a chewing gum, to combat the adverse health, physical, cosmetic and environmental effects of biofilms.

Biofilms are conglomerations of microorganisms that consist of one or more species of bacteria, fungi, algae, and protozoa, singly or as a mixture, in which the participants adhere together in an aqueous environment to form a film attached to surfaces or in free standing suspension. Secreting a glue-like substance not secreted as single cells in suspension, the organisms constituting biofilms can anchor to a wide variety of materials by extruding sisal-like filament attachments. Biological, organic, and inorganic surfaces are subject to biofilm formation. These surfaces include teeth, gums, human and animal blood vessels, medical implant materials, soil particles, metals, and plastics. Upon forming a biofilm, the participating organisms alter their morphology, behavior, and metabolism. Virtually any surface in contact with water is subject to the development of adhering biofilms. Alternatively, microorganisms can form biofilms as floating conglomerates similarly altering their characteristics.

When single species form biofilms, they differentiate, effectively becoming a multi-task community. In many instances, biofilms cause problems interfering with the normal operation, perhaps causing failure, of natural and artificial systems. The effects range from clogging capillary blood vessels in the circulatory system or brain that may lead to stroke, to causing prosthetic valve endocarditis, to constricting the effective diameter of stints surgically implanted to increase blood flow, to creating plaque and causing gingivitis in human or animal mouths, to clogging tubes and other plumbing in industrial equipment, to causing loss of efficiency in heat exchange systems. The total annual cost of these adverse consequences of biofilms runs into the billions of dollars.

More economic and specific measures to control biofilms are required. Many of the normal bio-control products, such as anti-microbials and disinfectants, are inadequate in combating many instances of biofilm infestation.

The U.S. Public Health Service Communicable Disease Center states that up to 65% of bacterial infections in humans are biofilms in nature. Furthermore, microorganisms that form biofilms then change their characteristics, sometimes drastically, such that doses of antibiotics which normally kill the organisms in suspended cultures are completely ineffective against the same microorganisms when the organisms are in attached or conglomerate biofilm form.

Biofilms play a key role in dental disease. Bacterial activity of over 500 different bacteria has been implicated in human dental plaque and in caries [Kolenbrander P. E., "Oral microbial communities: biofilms, interactions, and genetic systems", Annu. Rev. Microbiol., 54:413–437, 2000]. Adhesion of the bacteria to each other (intraspecies) and to other bacterial species (interspecies), as well as to oral surfaces, is one of the major factors leading to dental plaque and to caries and periodontal diseases.

Streptococci and actinomycetes are the major initial colonizers in forming dental biofilms. Their adhesion to the pellicle of salivary glycoproteins on tooth surfaces appears to be the first step in the formation of dental plaque [Kolenbrander P. E., "Oral microbial communities: biofilms, interactions, and genetic systems", Annu. Rev. Microbiol., 54:413–437, 2000]. Microorganisms that progressively accumulate thereafter, mostly gram negative anaerobic bacteria, in the gingival crevice area are the late colonizers and are believed to play a central role in the initiation and progression of periodontal diseases [Moore W. E., and Moore L. V., "The bacteria of periodontal diseases", Periodontol 2000, 5:66–77, 1994]. In this accumulative step, the bacteria coaggregate. The stability of plaque containing growing bacteria is a result of bacterial adhesion to the acquired pellicle, and, most importantly, of interspecies adhesion, the phenomenon of coaggregation. The bacterial species present in dental plaque are heterogeneous and they change progressively as the clinical condition goes from normal health through gingivitis to advanced stages of periodontitis. *Fusobacterium nucleatum* is the principal and most frequent cause of gingival inflammation that may initiate periodontal diseases, and it is also most commonly the predominant pathogen in subsequent periodontal destruction [Moore W. E., and Moore L. V., "The bacteria of periodontal diseases", Periodontol 2000, 5:66–77, 1994; Bolstad A. I., Jensen H. B., and Bakken V., "Taxonomy, biology, and periodontal aspects of *Fusobacterium nucleatum*", Clin. Microbiol. Rev., 9:55–71, 1996]. *F. nucleatum* plays a central role in providing physical bridges that mediate coaggregation of cells, thereby promoting anaerobic microenvironments that protect the coaggregating strict anaerobes [Kolenbrander P. E., "Oral microbial communities: biofilms, interactions, and genetic systems", Annu. Rev. Microbiol., 54:413–437, 2000; Kolenbrander P. E., and London J., "Adhere today, here tomorrow: oral bacterial adherence", J. Bacteriol., 175:3247–3252, 1993]. *F. nucleatum* coaggregates with many putative periodontal pathogens, such as *Porphyromonas gingivalis, Actinobacillus actinomycetemcomitans, Prevotella intermedius,* and certain species of *Treponema, Eubacterium,* and *Selenomonas*.

These periodontopathogens are also the prominent contributors to the formation of volatile sulfur compounds (VSC), the major components of halitosis [Quirynen M., Van Eldere J., Pauwels M., Bollen C. M., and van Steenberghe D., "In vitro volatile sulfur compound production of oral bacteria in different culture media", Quintessence Int., 30:351–356, 1999; Waler S. M., "On the transformation of sulfur-containing amino acids and peptides to volatile sulfur compounds (VSC) in the human mouth", Eur. J. Oral Sci., 105:534–537, 1997]. Unlike *P. gingivalis* that is usually absent in healthy gingival sulci, *F. nucleatum* is one of the dominant species not only in the lesions of periodontitis but also in gingivitis lesions and healthy gingival sites.

Dental plaque also contributes to tooth discoloration and to gingival irritation and subsequent periodontal disease. Current studies suggest that the periodontal diseases may trigger blood clots which can cause a heart attack or stroke [Wu T., Trevisan M., Genco R. J., Falkner K. L., Dorn J. P., and Sempos C. T., "Examination of the relation between periodontal health status and cardiovascular risk factors: serum total and high density lipoprotein cholesterol, C-reactive protein, and plasma fibrinogen", Am. J. Epidemiol., 151:273–282, 2000]. Once plaque bacteria enter the bloodstream through ulcerations in the gums, they may cause clots that then impede blood flow. The adhesions among bacteria and between or among bacteria and blood cells may be the mechanism. Hence, controlling plaque is expected to reduce the risk of developing such diseases.

*Streptococcus* can coaggregate and form biofilms on prosthetic heart valves. When heart valves are replaced, despite normal surgical care, endocarditis (infection of the valve) not infrequently occurs. A biofilm then develops, impairing the functioning of the valve. The principal treatment is replacement of the infected valve. While intravenous antimicrobial treatment has been attempted, it has largely been unsuccessful because of the protection the biofilm affords against penetration to the interior microbial cells that maintain the infection. When endocarditis occurs, some 70% of the time the results are fatal to the patient.

D-Galactose is known [Kolenbrander P. E., and Andersen R. N., "Inhibition of coaggregation between *Fusobacterium nucleatum* and *Porphyromonas* (*Bacteroides*) *gingivalis* by lactose and related sugars", Infect. Immun., 57:3204–3209, 1989; Shaniztki B., Hurwitz D., Smorodinsky N., Ganeshkumar N., and Weiss E. I., "Identification of a *Fusobacterium nucleatum* PK1594 galactose-binding adhesion which mediates coaggregation with periopathogenic bacteria and hemagglutination", Infect. Immun., 65:5231–5237, 1997] to reverse the coaggregations of oral bacteria that would otherwise form dental plaque. This property constitutes a distinct advantage if incorporated into toothpaste or mouthwash. D-Galactose, however, is low in the hygroscopicity required for toothpaste, is not sweet-tasting and does not have good mouthfeel.

D-Tagatose has been under development as a low-calorie, full-bulk sweetener for use in foods. It has also been under development for use in cosmetics, such as toothpaste and mouthwash. Generally Recognized As Safe (GRAS) status has been obtained for these uses.

SUMMARY OF THE INVENTION

In accordance with the broadest aspect of this invention, there is provided a method for disrupting biofilm and for inhibiting biofilm formation in an aqueous environment which comprises contacting said environment with an effective amount of D-tagatose.

It is an object of this invention to substitute, wholly or partially, tagatose for the sweeteners generally used in chewing gum, hard candies and other confections in order to counteract and prevent tooth, gum and other oral diseases caused by biofilms. In one aspect of the invention, tagotose replaces the monosaccharides, disaccharides and other sweeteners in chewing gum that promote the formation of biofilms. It is the further object to use tagatose in an effective amount to prevent the formation of biofilm caused by other sugars ingested in the diet. Biofilms formed from such sugars can be destroyed or removed by chewing of tagatose-containing gum. This is because the tagatose brought in contact with the teeth and gums will cause the constituent bacteria forming the biofilm to dissociate. Thus, regular use of tagatose-containing gum can prevent the formation of biofilms in the oral cavity, maintaining good oral health in an easy, pleasant manner. Applicable doses range from 0.1 to 1,000 g/Kg body weight administered as a health food, health drink, drug or cosmetic including toothpaste, mouthwash and lipstick.

Another aspect of the invention is to produce a chewing gum from a standard chewing gum base where the sweetener is D-tagatose. The D-tagatose can be the only sweetener in the chewing gum or can be used in combination with other sweeteners. Preferably the secondary sweeteners are non-nutrient sweeteners such as aspartame and saccharine.

In accordance with one aspect of this invention, the D-tagatose is used in toothpaste or mouthwash to attack dental plaque and to prevent the formation of such plaque, thereby improving oral health and hygiene. According to this aspect of the invention, the teeth are whitened through the removal of dental plaque, and oral diseases such as tooth caries or gingival and periodontal infections and halitosis are prevented or delayed through the removal of dental plaque. D-Tagatose may be the only humectant used in the toothpaste or it may constitute between about 10% and 90% of the humectant in the toothpaste.

In another application of this invention, D-tagatose is used in foodstuff to attack dental plaque and to prevent the formation of such plaque, thereby improving oral health and hygiene. The D-tagatose may also be administered in powder, crystalline or liquid form with or without other foodstuffs to disrupt dental plaque and to inhibit the formation of such plaque.

In accordance with another aspect of this invention, D-tagatose is administered orally to prevent or aid in the prevention of cardiovascular stroke, or to enhance the effectiveness of antibiotics administered to a patient in need of treatment for the prevention of cardiovascular stroke, or to a patient being administered antibiotics for other purposes. In accordance with this aspect of the invention, D-tagatose is preferably administered at a dose of between 10 and 500 mg/Kg of body weight. D-tagatose may be administered to a mammal subject in combination with a food, beverage or taken separately in powder, crystalline or liquid form to disrupt biofilm and for inhibiting biofilm formation in the body.

According to another aspect of this invention, the method for disrupting biofilm and for inhibiting biofilm formation in commercial and industrial water systems is to supply the water system with a solution of D-tagatose. Preferably, the solution is at a concentration of D-tagatose of between 100 and 1000 mM. Application may be continuous, intermittent or on demand.

DETAILED DESCRIPTION AND DEMONSTRATION OF THE INVENTION

Fifteen oral isolates, including both early colonizers (*Streptococcus* and *Actinomyces*) and late colonizers (*Fusobacterium, Porphyromonas, Prevotella, Veillonella, Capnocytophaga,* and *Actinobacillus*), were tested for their ability to coaggregate with each other, followed by testing for the reversal of coaggregation by the addition of D-tagatose. Bacterial strains used were of human gingival crevice origin. The coaggregation was examined visually by a scoring system ranging from 0 for no visible coaggregation to 4 for maximum coaggregation [Cisar J. O., Kolenbrander P. E., and McIntire F. C., "Specificity of coaggregation reactions between human oral streptococci and strains of *Actinomyces viscosus* or *Actinomyces naeslundii*", Infect. Immun., 24:742–752. 1979]. D-Tagatose, at a concentration of less than 750 mM, completely reversed the coaggregation of 17 (60%) of 28 strong coaggregating pairs (with a coaggregation score of 2 or higher) tested. In contrast, D-sorbitol had little or no effect on the coaggregating pairs tested. These D-tagatose sensitive coaggregations were D-galactose reversible as well. D-Tagatose acted on both early colonizers and late colonizers that were gram-negative anaerobes frequently involved periodontal diseases.

Pairs of various species of oral bacteria were tested for coaggregation, and for reversal of coaggregation when D-tagatose or D-galactose was administered. The scored results are shown in Table 1.

TABLE 1 interspecies coaggregation of oral bacteria†

| | SO34 | Cl04 | J22 | PK509 | T14V | PK29 | PK947 | PK1594 | PK1924 | PK1295 | PK1910 | Capno 4 | Capno 25 | Capno 27 | JP2 |
|---|---|---|---|---|---|---|---|---|---|---|---|---|---|---|---|
| Streptococcus oralis SO34 | | 0 | 0 | 2* | 0 | 4* | 3* | 4 | 0 | 4* | 3* | 0 | 0 | 0 | 0 |
| Streptococcus oralis Cl04 | | | 0 | 3* | 0 | 4* | 2* | 4 | 0 | 4* | 3* | 0 | 0 | 0 | 0 |
| Streptococcus mutis J22 | | | | 0 | 4 | 4* | 2* | 4 | 0 | 3* | 2 | 0 | 0 | 0 | 0 |
| Streptococcus morbillorum PK509 | | | | | 0 | 2* | 0 | 4 | 0 | 2* | 2* | 0 | 0 | 0 | 0 |
| Actinomyces naeslundii T14V | | | | | | 0 | 0 | 4 | 0 | 0 | 0 | 0 | 0 | 0 | 0 |
| Actinomyces naeslundii PK29 | | | | | | | 0 | 4 | 0 | 0 | 1 | 0 | 0 | 0 | 0 |
| Actinomyces naeslundii PK947 | | | | | | | | 4 | 0 | 0 | 0 | 0 | 0 | 0 | 0 |
| Fusobacterium nucleatum PK1594 | | | | | | | | | 4* | 0 | 3* | 0 | 1* | 0 | 3* |
| Porphyromonas gingivalis PK1924 | | | | | | | | | | 0 | 0 | 0 | 0 | 0 | 0 |
| Prevotella loescheii PK1295 | | | | | | | | | | | 0 | 0 | 0 | 0 | 0 |
| Veillonella atypica PK1910 | | | | | | | | | | | | 0 | 0 | 0 | 0 |
| Capnocytophaga sputigena 4 | | | | | | | | | | | | | 0 | 0 | 0 |
| Capnocytophaga ochracea 25 | | | | | | | | | | | | | | 0 | 0 |
| Capnocytophaga gingivalis 27 | | | | | | | | | | | | | | | 0 |
| Actinobacillus actinomycetemcomitans JP2 | | | | | | | | | | | | | | | |

†Each bacterial pair was visually examined for coaggregation and given a coaggregation score by a scoring system ranging from 0 for no visible coaggregation to 4 for maximum coaggregation.
*Coaggregations were reversed by both D-galactose and D-tagatose.

Phase-contrast photomicrographs of coaggregation between *F. nucleatum* PK1594 and *P. gingivalis* PK1924 showed that the addition of D-galatose (143 mM final concentration) dissociates clumps into individual cells, and that D-tagatose also dissociates the clumps into individual cells although a higher concentration is required (400 mM final concentration), but, at an equal concentration (400 mM final concentration), D-sorbitol did not dissociate the clumps.

Table 2 compares D-galactose, D-tagatose and D-sorbitol for plaque reversibility, demonstrating that D-tagatose has an effect, although at somewhat higher concentrations, virtually equal to that of D-galactose, but that D-sorbitol, at similarly higher concentrations, is markedly inferior in this characteristic.

TABLE 2

The reversibility comparison among D-galactose, D-tagatose and D-sorbitol†

| | Water | D-Galactose | | D-Tagatose | | D-Sorbitol | |
|---|---|---|---|---|---|---|---|
| Pairs | Score | Conc. mM | Score | Conc. mM | Score | Conc. mM | Score |
| PK509/PK1295 | 2 | 143 | 0 | 600 | 0 | 600 | 0 |
| PK509/PK1910 | 2 | 143 | 0 | 400 | 0 | 400 | 0 |
| PK29/SO34 | 4 | 143 | 1 | 750 | 1 | 750 | 4 |
| PK29/C104 | 4 | 143 | 1 | 750 | 1 | 750 | 4 |
| PK29/J22 | 4 | 143 | 1 | 750 | 1 | 750 | 4 |
| PK29/PK509 | 2 | 143 | 0 | 200 | 0 | 200 | 2 |
| PK947/SO34 | 3 | 143 | 0 | 200 | 0 | 200 | 2 |
| PK947/C104 | 2 | 143 | 0 | 200 | 0 | 200 | 1 |
| PK947/J22 | 2 | 143 | 0 | 200 | 0 | 200 | 2 |
| PK1594/PK1924 | 4 | 143 | 0 | 400 | 0 | 400 | 3 |
| PK1594/PK1910 | 3 | 143 | 0 | 200 | 0 | 200 | 1 |
| PK1594/JP2 | 3 | 143 | 1 | 600 | 0 | 600 | 2 |
| PK509/SO34 | 2 | 143 | 0 | 400 | 1 | 400 | 1 |
| PK509/C104 | 3 | 143 | 0 | 750 | 1 | 750 | 1 |
| PK1295/SO34 | 4 | 143 | 0 | 750 | 1 | 750 | 1 |
| PK1295/C104 | 4 | 143 | 1 | 750 | 2 | 750 | 2 |
| PK1295/J22 | 4 | 143 | 0 | 750 | 2 | 750 | 2 |

TABLE 2-continued

The reversibility comparison among D-galactose, D-tagatose and D-sorbitol†

| Pairs | Water Score | D-Galactose Conc. mM | Score | D-Tagatose Conc. mM | Score | D-Sorbitol Conc. mM | Score |
|---|---|---|---|---|---|---|---|
| PK1910/SO34 | 3 | 143 | 1 | 200 | 1 | 200 | 1 |
| PK1910/C104 | 3 | 143 | 0 | 200 | 1 | 200 | 1 |

†Each bacterial pair was visually examined for coaggregation and given a coaggregation score by a scoring system ranging from 0 for no visible coaggregation to 4 for maximum coaggregation. The highest sugar concentration used was 750 mM.
The bacterial strains used here were *Streptococcus oralis* SO34, *Streptococcus oralis* C104, *Streptococcus mitis* J22, *Streptococcus morbillorum* PK509, *Actinomyces naeslundii* PK29, *Actinomyces naeslundii* PK947, *Fusobacterium nucleatum* PK1594, *Porphyromonas gingivalis* PK1924, *Prevotella loescheii* PK1295, *Veillonella atypica* PK1910 and *Actinobacillus actinomycetemcomitans* JP2.

Thus, D-tagatose is demonstrated to have the potential for preventing plaque development and for disassembling existing plaque by altering the subgingival microbiota, resulting in conservative control of gingival and periodontal disease, and halitosis.

The commercial and industrial water systems to which the D-tagatose may be added to disrupt biofilm and to inhibit biofilm formation include cooling waters; food, beverage and industrial process waters; pulp and paper mill systems; milk processing, brewery pasteurizers; sweetwater systems; air washer systems; oil field drilling fluids and muds; petroleum recovery processes; industrial lubricants; cutting fluids; heat transfer systems; gas scrubber systems; latex systems; clay and pigment systems; decorative fountains; water intake pipes; ballast water tanks; and ship reservoirs. Other systems include power plant water intakes, wet chemistry analytical equipment, kidney dialysis membranes and coils, stints, and other implants in humans and animals, engines, and the cleansing of medical instruments prior to autoclaving.

EXAMPLE 1

Use of D-tagatose in Toothpaste to Control Dental Plaque and Associated Oral Pathology:

TABLE 3

A toothpaste formula (% wt/wt)

| Component | |
|---|---|
| D-Sorbitol | 10.447 |
| D-Tagatose | 10.450 |
| Glycerin | 7.000 |
| Polyethylene glycol | 4.000 |
| Water (aqua), deionized | 33.700 |
| Sodium fluoride | 0.243 |
| Sodium saccharin | 0.100 |
| Monosodium phosphate | 0.415 |
| Trisodium phosphate | 0.395 |
| Titanium dioxide | 0 500 |
| Sodium carboxymethyl cellulose | 0 750 |
| Amorphous silica | 30 000 |
| Sodium lauryl sulfate | 1.200 |
| Spearmint oil | 0.800 |

A toothpaste is prepared using the formula shown in Table 3. The toothpaste is used in normal fashion, preferably 2 to 3 times per day, and preferably after eating. The toothpaste functions well and has an excellent taste. Inclusion of the D-tagatose causes a separation of early colonizers and the late colonizers, rendering the tooth enamel accessible to cleaning by the dentifrice. The D-tagatose also prevents the formation of new plaque by inhibiting coaggregation of plaque-forming species. Regular use of the toothpaste maintains a healthy environment in the mouth, thereby preventing or delaying oral disease, including caries, gingival and periodontal diseases, and halitosis, and, at the same time, reducing the risk of heart attack or stroke.

EXAMPLE 2

Use of D-Tagatose in a Mouthwash to Control Dental Plaque and Associated Oral Pathology:

TABLE 4

A mouthwash formula.

| Component | |
|---|---|
| Alcohol | 10% v/v |
| D-Tagatose | 10% w/v |
| Pluronic F-127 surfactant | 0.75% w/v |
| Sodium chloride | 0.5845% w/v |
| Sodium saccharin | 0.10% w/v |
| Menthol | 0.13% w/v |
| Peppermint oil | 0.09% w/v |
| Tetrasodium ethylenediaminetetraacetic acid | 0.0114% w/v |
| Butylated hydroxyanisole | 0.0005% w/v |
| Citric acid, anhydrous | 0.0525% w/v |
| FD & C Blue #1 | 0.0003% w/v |
| Sodium ricinoleate | 1% w/v |
| Distilled water | q.s |

A mouthwash solution is prepared using the formula shown in Table 4. Several milliliters of the mouthwash are used to rinse the teeth and gums two to three times per day, and/or whenever mouth refreshment is desired. The applications may or may not follow brushing of the teeth. The mouthwash has excellent taste and mouthfeel. Inclusion of the D-tagatose reduces existing plaque on the teeth by removing the late colonizers, and by exposing the early colonizers to the dentifrice used in brushing. The D-tagatose also prevents the formation of new plaque by inhibiting coaggregation of plaque-forming species. Regular use of the mouthwash maintains a healthy environment in the mouth, thereby preventing or delaying oral disease, including carries, gingival and periodontal diseases, and halitosis, and, at the same time, reducing the risk of heart attack or stroke.

EXAMPLE 3

Use of D-Tagatose in Foods to Control Dental Plaque and Oral Pathology:

Forty subjects, half male, half female, ranging from 4 to 80 years in age, daily consume foodstuffs, such as cakes, cookies, pies, hard candy, hot and cold cereals, cold fruit drinks, iced tea, coffee and tea, that are sweetened with conventional sweeteners including sucrose and high fructose corn syrup (HFCS). After several monthly check-ups, these subjects are found to have high dental plaque indices, and many of them are diagnosed with plaque-related oral diseases. At this point, the test foodstuffs are switched such that D-tagatose is used as a one-for-one replacement for the table sugar and HFCS previously used. No other changes are made in the test regimen. By the third monthly check-up, the subjects' plaque indices are significantly lowered, and those who formerly exhibited plaque-related oral diseases show complete or nearly complete recovery.

EXAMPLE 4

Use of D-Tagatose in Enhancing Antibiotic Activity:

A patient with a *staphylococcus* lesion of the leg is placed on oral penicillin by her physician. However, the desired curative effect does not take place. The formation of plaque in the infected region protects the interior microorganisms from the antibiotic coursing through the bloodstream, and the plaque organisms develop increased resistance. The physician prescribes five grams of D-tagatose be taken with each of three meals daily, along with continued taking of the penicillin. After one day, the antibiotic becomes effective, and in the course of a week the lesion disappears, and the patient is cured.

EXAMPLE 5

Prophylaxis Against Prosthetic Valve Endocarditis:

An adult female patient requires removal of her infected mitral valve and its replacement with a prosthetic valve. One of the principal hazards of such an operation is that the valve region of the heart will become infected, frequently with streptococci that form a biofilm protecting internal microorganisms from antibiotics, and also permitting such organisms to develop increasing resistance. In order to prevent the buildup of a biofilm infection, the physician places his patient on tagatose treatment for three days prior to the surgery. On each such day, the patient consumes 10 grams of D-tagatose with each of her three daily meals. The resulting D-tagatose blood level is sufficient to preclude the formation of a biofilm on the heart valve. The treatment is continued until one week after the operation and the patient is well on the road to recovery. Infection has been avoided.

EXAMPLE 6

Prevention of Stroke:

A patient has gradually developed high blood pressure over the years. His doctor places him on a blood pressure medicine when his pressure reaches 135/90 mm Hg. Despite gradual increases in dosage of the medicine, and trials of new medicines, over time his blood pressure continues to increase until reaching 145/100 mm Hg. At this point the physician fears the possibility of a stroke. Knowing that strokes are frequently caused by the formation of plaques in the bloodstream that migrate to the brain, the physician institutes a regimen in which the patient takes 5 grams of D-tagatose with each of three daily meals, while continuing to take his other medication. By dispersing plaques that may already have formed in the bloodstream, and by preventing formation of new plaques, the risk of stroke is significantly reduced.

EXAMPLE 7

Sterilization of Food-Handling Machinery:

A cheese-making plant processes raw milk into cheese. The equipment includes many tubes, tubules, pipes and other surfaces that come in direct contact with the milk. Between runs, standard "Clean-In-Place" (CIP) operations are performed in which acid and oxidants are coursed through the equipment to contact all surfaces and are then washed out with sterile water. However, the formation of microbial plaques protects the microorganisms in the interiors of the plaques, and some survive the CIP. To overcome this problem, an initial step is added to the CIP whereby a stream of 200 mM D-tagatose in sterile water is run through the equipment, contacting all surfaces, immediately prior to instituting the CIP. This initial treatment is successful in reducing the total bacteria and the coliform counts to acceptable regulatory levels. Accordingly, the D-tagatose wash is made part of the CIP.

EXAMPLE 8

A typical commercial spearmint chewing gum was prepared, but completely substituting tagatose for the fructose normally used in the gum. Tagatose thus constituted 50% of the original weight of the gum. The gum was tested and found to be pleasant to the taste. A piece of the gum was placed into a suspension of two species of coaggregated bacteria (forming a biofilm). The suspension was agitated for 30 seconds and a drop of the suspension was removed and a photomicrograph was taken. After 6 hours incubation at 37° C., the suspension was shaken and another drop removed and a photomicrograph was taken. Comparison of the two photomicrographs showed that the co-aggregations of the bacteria had been almost completely disrupted, terminating the biofilm. A control experiment with fructose-based gum showed that the bacterial population had increased after the 6-hour incubation period, and the co-aggregations had also increased in number and density.

EXAMPLE 9

Hard candy was made with a 50% tagatose content and no other sweetener. The same type of experiment described in Example 8 was run. The results confirmed the benefit of using tagatose in the hard candy in that it destroyed the biofilm while the control candy containing fructose caused an increase in the amount and density of biofilm.

We claim:

1. A method for disrupting biofilm and for inhibiting biofilm formation in commercial and industrial water systems comprising the steps of contacting water systems with aqueous solutions of D-tagatose.

2. The method of claim 1 wherein the concentration of D-tagatose in the solution is between 100 and 1,000 mM.

* * * * *